(12) United States Patent
Lozanov et al.

(10) Patent No.: US 8,884,046 B2
(45) Date of Patent: Nov. 11, 2014

(54) COMPOUNDS USEFUL IN THE SYNTHESIS OF BENZAMIDE COMPOUNDS

(71) Applicants: Mario Emilov Lozanov, Baton Rouge, LA (US); Anthony Frank Skufca, Zachary, LA (US); Andrew George Zeiler, Kalamazoo, MI (US)

(72) Inventors: Mario Emilov Lozanov, Baton Rouge, LA (US); Anthony Frank Skufca, Zachary, LA (US); Andrew George Zeiler, Kalamazoo, MI (US)

(73) Assignee: Resverlogix Corp., Calgary, Alberta (CA)

( * ) Notice: Subject to any disclaimer, the term of this patent is extended or adjusted under 35 U.S.C. 154(b) by 0 days.

(21) Appl. No.: 14/050,076

(22) Filed: Oct. 9, 2013

(65) Prior Publication Data
US 2014/0107369 A1    Apr. 17, 2014

Related U.S. Application Data

(60) Provisional application No. 61/713,711, filed on Oct. 15, 2012.

(51) Int. Cl.
*C07C 255/59*    (2006.01)
*C07C 235/38*    (2006.01)
*C07C 255/60*    (2006.01)

(52) U.S. Cl.
CPC ............. *C07C 255/59* (2013.01); *C07C 235/38* (2013.01); *C07C 255/60* (2013.01)
USPC ............................ 558/414; 564/214; 558/418

(58) Field of Classification Search
CPC .... C07C 235/38; C07C 255/59; C07C 255/60
USPC .................... 558/418, 414; 564/214
See application file for complete search history.

(56) References Cited

U.S. PATENT DOCUMENTS

| | | | |
|---|---|---|---|
| 7,846,915 | B2 | 12/2010 | Wong et al. |
| 8,053,440 | B2 | 11/2011 | Hansen |
| 8,093,273 | B2 | 1/2012 | Wong et al. |
| 8,114,995 | B2 | 2/2012 | Hansen et al. |
| 8,242,130 | B2 | 8/2012 | Wong et al. |
| 8,242,144 | B2 | 8/2012 | Wong et al. |
| 8,410,109 | B2 | 4/2013 | Wong et al. |
| 2004/0033480 | A1 | 2/2004 | Wong |
| 2005/0080021 | A1 | 4/2005 | Tucker et al. |
| 2005/0080024 | A1 | 4/2005 | Tucker et al. |
| 2007/0099826 | A1 | 5/2007 | Wong et al. |
| 2011/0294807 | A1 | 12/2011 | Hansen |
| 2012/0015905 | A1 | 1/2012 | Hansen |
| 2012/0040954 | A1 | 2/2012 | Hansen |
| 2012/0059002 | A1 | 3/2012 | Hansen et al. |
| 2013/0108672 | A1 | 5/2013 | Shenoy |

FOREIGN PATENT DOCUMENTS

| | | |
|---|---|---|
| CA | 2 676 984 A1 | 8/2008 |
| CA | 2 815 127 A1 | 4/2012 |
| WO | WO 2008/092231 A1 | 8/2008 |

OTHER PUBLICATIONS

International Search Report and Written Opinion mailed May 28, 2014, in International Application No. PCT/IB2013/003031, filed Oct. 9, 2013 by Resverlogix Corp.
Mitchell et al., "Bromination of 4,6-dimethoxyindoles" *Tetrahedron*, 68(39):8163-8171 (2012).

*Primary Examiner* — Samantha Shterengarts
*Assistant Examiner* — Amanda L Aguirre
(74) *Attorney, Agent, or Firm* — Finnegan, Henderson, Farabow, Garrett & Dunner, LLP

(57) ABSTRACT

Compounds that are useful in the synthesis of 2-amino-4,6-dimethoxybenzamide derivatives and other benzamide compounds.

15 Claims, No Drawings

COMPOUNDS USEFUL IN THE SYNTHESIS OF BENZAMIDE COMPOUNDS

This application claims priority from U.S. Provisional Patent Application No. 61/713,711, filed Oct. 15, 2012, and is incorporated herein by reference in its entirety.

TECHNICAL FIELD

This invention relates to novel compounds useful in the synthesis of benzamide compounds.

BACKGROUND

Benzamide compounds have been involved as intermediates for the synthesis of many pharmaceutical therapeutic drugs. For example, 2-amino-4,6-dimethoxybenzamide was reported as an intermediate in U.S. Pat. No. 3,966,965 in the synthesis of oxamic acid derivatives for the prevention of hypersensitivity in allergic reactions. More recent patent applications describe this compound as a valuable intermediate en route to new cardiovascular agents (US2008/0188467 and WO2008/92231 to Resverlogix Corp).

2-Amino-4,6-dimethoxybenzamide can be prepared from 4,6-dimethoxyisatoic anhydride. The 4,6-dimethoxyisatoic anhydride may be prepared by a reaction of 4,6-dimethoxyanthranilic acid with phosgene (U.S. Pat. No. 4,191,840 and Org. Synth. 1947, 27, 45). Alternatively, to prepare 2-amino-4,6-dimethoxybenzamide, 3,5-dimethoxyaniline may be converted to its hydrochloride salt, after which the salt is reacted with oxalyl chloride to give 4,6-dimethoxyisatin. The isatin may then be converted to the target compound via an unstable carboxyl intermediate by reaction with sodium hydroxide and hydrogen peroxide followed by an EDCl/HOBt-mediated coupling to form 2-amino-4,6-dimethoxybenzamide (WO2008/92231).

Previously known methods for the synthesis of benzamide compounds and derivatives often involved unstable intermediates, inefficient processes, and in some cases, a large number of steps, resulting in lower yields and increased costs of manufacturing. Thus, there is a continuing need for methods to make benzamide compounds and derivatives that are efficient, do not require the use of exotic or unstable reagents, use low-cost reagents, and provide environmentally streamlined processes.

DISCLOSURE OF THE INVENTION

The invention provides novel compounds that are useful in a method of synthesizing benzamide compounds. In one aspect, the invention provides a method to make benzamide compounds using low-cost reagents. More specifically, the compounds of the invention may be used in methods for the synthesis of benzamide compounds comprising fewer and/or more efficient reaction steps, fewer isolations, higher yields, and improved purity. These and other features of the invention will be apparent from the ensuing description, drawings, and appended claims.

In some embodiments, the compounds of the invention are selected from compounds of Formula I:

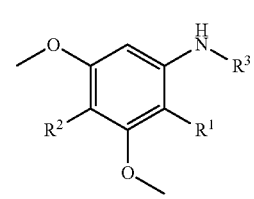

Formula I wherein:
  $R^1$ is selected from Br and CN;
  $R^2$ is selected from H and Br;
  $R^3$ is selected from H and

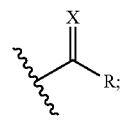

wherein
  R is selected from H, $CH_3$, $CF_3$, $CF_2H$, $CFH_2$, $CCl_3$, $CCl_2H$, $CClH_2$, $CBr_3$, $CBr_2H$, and $CBrH_2$; and
  X is selected from O and S;
with the proviso that:
  when $R^1$ is Br and $R^2$ is H, then R is not $CH_3$;
  when $R^1$ is CN then $R^2$ is H; and
  when $R^1$ is Br then $R^3$ is

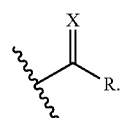

In some embodiments, the compounds of the invention are selected from compounds of Formula I-A:

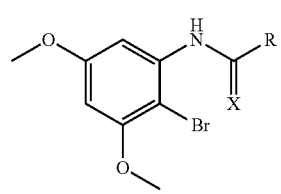

Formula I-A wherein:
  R is selected from H, $CF_3$, $CF_2H$, $CFH_2$, $CCl_3$, $CCl_2H$, $CClH_2$, $CBr_3$, $CBr_2H$, and $CBrH_2$; and
  X is selected from O and S.

In other embodiment, the compounds of the invention are selected from compounds of Formula I-B

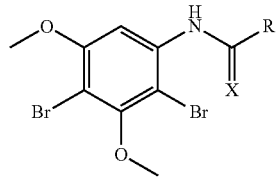

Formula I-B wherein:
R is selected from H, CH$_3$, CF$_3$, CF$_2$H, CFH$_2$, CCl$_3$, CCl$_2$H, CClH$_2$, CBr$_3$, CBr$_2$H, and CBrH$_2$; and
X is selected from O and S.

In other embodiments, the compounds of the invention are selected from compounds of Formula I-C:

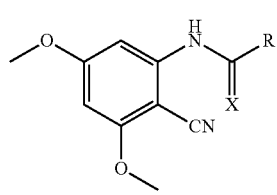

Formula I-C wherein:
R is selected from H, CH$_3$, CF$_3$, CF$_2$H, CFH$_2$, CCl$_3$, CCl$_2$H, CClH$_2$, CBr$_3$, CBr$_2$H, and CBrH$_2$; and
X is selected from O and S.

In a specific embodiment, the compound of the present invention is

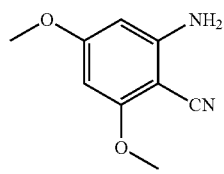

(2-Amino-4,6-dimethoxybenzonitrile).

In some embodiments, the compounds of the invention are selected from compounds of formula I-A, wherein X is oxygen.

In other embodiments, the compounds of the invention are selected from compounds of formula I-B, wherein X is oxygen.

In other embodiments, the compounds of the invention are selected from compounds of formula I-C, wherein X is oxygen.

In some embodiments, the compounds of the invention are selected from compounds of formula I-A, wherein R is selected from CF$_3$, CF$_2$H, CFH$_2$, CCl$_3$, CCl$_2$H, and CClH$_2$.

In some embodiments, the compounds of the invention are selected from compounds of formula I-B, wherein R is selected from CF$_3$, CF$_2$H, CFH$_2$, CCl$_3$, CCl$_2$H, and CClH$_2$.

In some embodiments, the compounds of the invention are selected from compounds of formula I-C, wherein R is selected from CF$_3$, CF$_2$H, CFH$_2$, CCl$_3$, CCl$_2$H, and CClH$_2$.

EMBODIMENTS OF THE INVENTION

The invention provides compounds useful in the synthesis of 2-amino-4,6-dimethoxybenzamide and other benzamide compounds.

In some embodiments the compounds of the invention are produced by the following methods:
(i) protecting 3,5-dimethoxyaniline with a protecting agent to form a protected 3,5-dimethoxyaniline,
(ii) halogenating the protected 3,5-dimethoxyaniline with a halogenating agent to form a halogenated protected 3,5-dimethoxyaniline,
(iii) cyanating the halogenated protected 3,5-dimethoxyaniline with a cyanating agent to form a cyanated protected 3,5-dimethoxyaniline,
(iv) deprotecting the cyanated protected 3,5-dimethoxyaniline to form a cyanated 3,5-dimethoxyaniline,
(v) crystallizing the cyanated 3,5-dimethoxyaniline, and
(vi) hydrating the cyanated 3,5-dimethoxyaniline to form 2-amino-4,6-dimethoxybenzamide.

Depending on the starting compound and the desired benzamide compound to be synthesized, certain functional groups may need to be protected. One skilled in the art may use any known methods to protect certain functional group(s) from unwanted reaction during the steps of halogenation, cyanation, and/or hydration.

In some embodiments, the compounds of the invention are selected from:

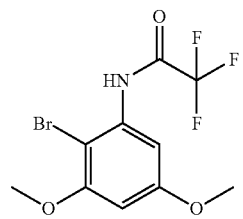

A 2-bromo-3,5-dimethoxytrifluoroacetanilide [A],

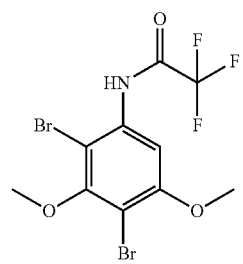

B 2,4-dibromo-3,5-dimethoxytrifluoroacetanilide [B],

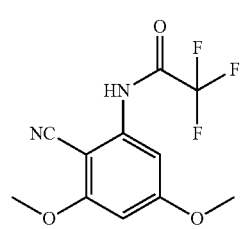

C 2-cyano-3,5-dimethoxytrifluoroacetanilide [C], and

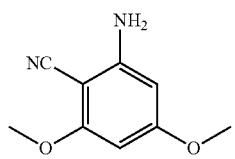

2-amino-4,6-dimethoxybenzonitrile [D].

In one example, the synthesis of 2-amino-4,6-dimethoxybenzamide comprises protecting 3,5-dimethoxyaniline with at least one protecting agent to form a protected aniline compound. The protecting step comprises reacting 3,5-dimethoxyaniline with a protecting agent such as trifluoroacetic anhydride using triethylamine in toluene to form a protected aniline compound, or in this example 3,5-dimethoxyaniline forms 3,5-dimethoxytrifluoroacetanilide. In one embodiment, a solution comprising the toluene is taken directly to the next step—the halogenation step—following aqueous washes. In another embodiment, a solution comprising the toluene is taken directly to the next step—the halogenation step—without aqueous washes.

Alternatively, one skilled in the art may remove, reduce, or increase the amount of toluene and/or other intermediates, and/or remove water before halogenating the compound, such as, for example, removal of water via azeotropic distillation of toluene and water. Though one embodiment of a protecting group in this example is trifluoroacetyl to protect the NH2 functional group of the aniline compound, other protecting groups such as acetyl, various monohaloacetyl, dihaloacetyl, and trihaloacetyl may also be used. It has been discovered that the trifluoroacetyl protecting group results in an improved selectivity during the halogenation process step over the acetyl protecting group.

In some embodiments, the invention provides a compound of Formula I-A:

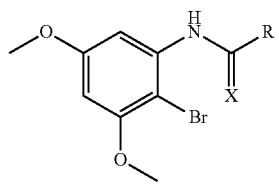

Formula I-A wherein:
R is selected from H, $CF_3$, $CF_2H$, $CFH_2$, $CCl_3$, $CCl_2H$, $CClH_2$, $CBr_3$, $CBr_2H$, and $CBrH_2$; and
X is selected from O and S.

In some embodiments, the invention provides a compound of Formula I-B:

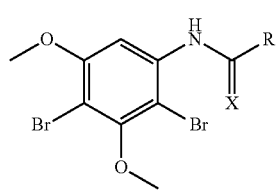

Formula I-B wherein:
R is selected from H, $CH_3$, $CF_3$, $CF_2H$, $CFH_2$, $CCl_3$, $CCl_2H$, $CClH_2$, $CBr_3$, $CBr_2H$, and $CBrH_2$; and
X is selected from O and S.

In some embodiments, the invention provides a compound of Formula I-C:

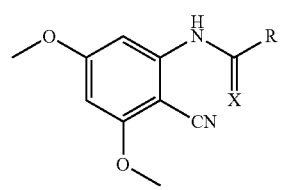

Formula I-C wherein:
R is selected from H, $CH_3$, $CF_3$, $CF_2H$, $CFH_2$, $CCl_3$, $CCl_2H$, $CClH_2$, $CBr_3$, $CBr_2H$, and $CBrH_2$; and
X is selected from O and S.

In some embodiments, the compound of the invention is selected from:
2-bromo-3,5-dimethoxytrifluoroacetanilide,
2,4-dibromo-3,5-dimethoxytrifluoroacetanilide,
2-cyano-3,5-dimethoxytrifuoroacetanilide, and
2-amino-4,6-dimethoxybenzonitrile.

In some embodiments, the invention provides a compound according to Formula I-A:

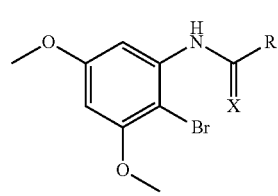

Formula I-A wherein:
R is selected from H, $CF_3$, $CF_2H$, $CFH_2$, $CCl_3$, $CCl_2H$, $CClH_2$, $CBr_3$, $CBr_2H$, and $CBrH_2$; and
X is O.

In some embodiments, the invention provides a compound according to Formula I-B:

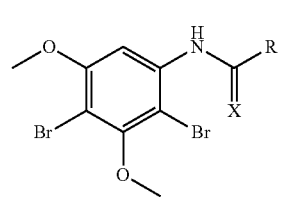

Formula I-B wherein:
R is selected from H, $CH_3$, $CF_3$, $CF_2H$, $CFH_2$, $CCl_3$, $CCl_2H$, $CClH_2$, $CBr_3$, $CBr_2H$, and $CBrH_2$; and
X is O.

In some embodiments, the invention provides a compound according to Formula I-C:

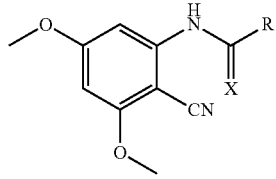

Formula I-C wherein:
R is selected from H, CH₃, CF₃, CF₂H, CFH₂, CCl₃, CCl₂H, CClH₂, CBr₃, CBr₂H, and CBrH₂; and
X is O.

In some embodiments, the invention provides a compound according to Formula I-A:

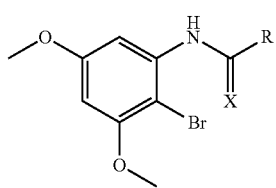

Formula I-A wherein:
R is selected from CF₃, CF₂H, CFH₂, CCl₃, CCl2$_H$, and CClH₂; and
X is selected from O and S.

In some embodiments, the invention provides a compound according to Formula I-B:

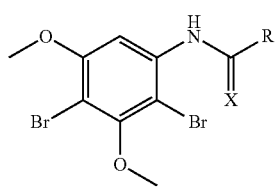

Formula I-B wherein:
R is selected from CF₃, CF₂H, CFH₂, CCl₃, CCl₂H, and CClH₂; and
X is selected from O and S.

In some embodiments, the invention provides a compound according to Formula I-C:

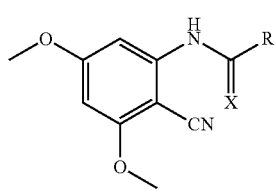

Formula I-C wherein:
R is selected from CF₃, CF₂H, CFH₂, CCl₃, CCl₂H, and CClH₂; and
X is selected from O and S.

The following examples are presented for purposes of illustration, and are not intended to impose limitations on the scope of this invention.

Example 1

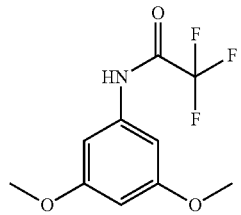 [SMILES: COc1cc(NC(=O)C(F)(F)F)cc(OC)c1]

3,5-dimethoxytrifluoroacetanilide

To a 2-L jacketed flask was loaded 3,5-dimethoxyaniline (120 g), toluene (1335 g), and triethylamine (87 g). The mixture was stirred at 18-20° C. until all solids had dissolved. Trifluoroacetic anhydride (185 g) was added over at least 1 h, maintaining a reaction temperature of 18-25° C. The reaction was stirred for at least 1 h and then checked by HPLC for reaction completion. Water (250 g) was loaded to the batch and the reaction was heated to 40-45° C. and stirred for at least 10 min. The agitation was stopped and the phases separated. The bottom aqueous phase was removed and water (250 g) was loaded to the toluene product layer. The batch was stirred at 40-45° C. for at least 10 min and the phases were separated by removing the bottom aqueous phase. The 3,5-dimethoxytrifluoroacetanilide product toluene solution was then cooled to below 0° C. in preparation for the bromo-3,5-dimethoxytrifluoroacetanilide step of the process. ¹H-NMR (Acetone-d₆): d 10.10 (br s, 1H), 6.97 (d, J=2.1 Hz, 2H), 6.38 (m, 1H), 3.77 (s, 6H). GC-MS: 249.15.

Example 2

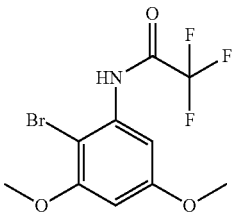

A

2-Bromo-3,5-dimethoxytrifluoroacetanilide [A]

The 3,5-dimethoxytrifluoroacetanilide toluene solution contained in a 2-L jacketed flask was cooled to −5 to 0° C. N-bromosuccinimide solid (145 g) was loaded to the cold 3,5-dimethoxytrifluoroacetanilide slurry in 5-10 g portions over the course of at least 1 h. A temperature of less than 0° C. was maintained during the addition. Upon completion of the addition, the batch was allowed to warm to 15-23° C. and was stirred for at least 1 h. The reaction completion was monitored by HPLC. When the reaction was complete, water (235 g) was loaded to the batch and the reaction heated to 35-45° C. and held for at least 10 min. The agitation was stopped and the phases were allowed to separate. The bottom aqueous phase was removed and water (235 g) was loaded to the bromo-3,5-dimethoxytrifluoroacetanilide toluene solution. The batch was agitated at 35-45° C. for at least 10 min and the phases were separated by removal of the lower aqueous phase. The 2-bromo-3,5-dimethoxytrifluoroacetanilide toluene solution was transferred to a 2-L four-neck round bottom flask fitted with a distillation apparatus and a heating mantle. The solution was heated to reflux and toluene was distilled until a pot temperature of 125-140° C. was obtained. The batch was cooled to less than 80° C. under nitrogen and N,N'-dimethylformamide (DMF; 1215 g) was loaded to the pot. The batch was agitated and cooled to less than 80° C. This solution was used in the 2-amino-4,6-dimethoxybenzonitrile step of the process. $^1$H NMR (acetone-$d_6$) δ 9.69 (br s, 1H), 7.05 (d, J=2.7 Hz, 1H), 6.66 (d, J=2.6 Hz, 1H), 3.93 (s, 3H), 3.85 (S, 3H); $^{13}$C NMR (acetone-$d_6$) δ 161.2, 158.2, 156.0 (q, J=37.3 Hz), 138.2, 117.0 (q, J=288 Hz), 104.1, 99.2, 98.6, 57.0, 56.2.

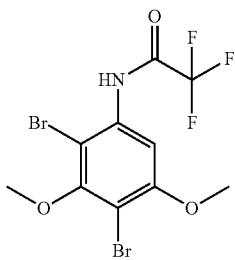

2,4-Dibromo-3,5-dimethoxytrifluoroacetanilide [B]

Compound B can be isolated as a useful byproduct from the synthesis of compound A by, for example, chromatography. GC-MS m/z 407.00 (m), 328 (m-Br).

Example 3

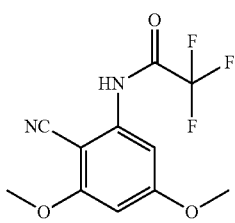

2-cyano-3,5-dimethoxytrifluoroacetanilide [C]

To the 2-bromo-3,5-dimethoxytrifluoroacetanilide/DMF solution in a 2-L round bottom flask was loaded 89 g of copper cyanide (CuCN). The batch was heated to 98-120° C. and held for at least 6 h. Reaction completion was checked using HPLC analysis. Upon completion, the reaction was cooled to less than 60° C. and vacuum was applied to the vessel and DMF was distilled. The distillation was continued to a pot volume of approximately 570 mL. The pot residue was cooled to less than 40° C. $^1$H NMR (DMSO-$d_6$) δ 11.63 (br s, 1H), 6.69 (s, 2H), 3.91 (s, 3H), 3.85 (s, 3H). GC-MS: 274.15 (m).

Example 4

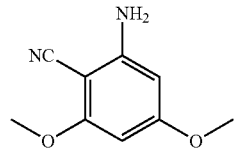

2-amino-4,6-dimethoxybenzonitrile [D]

To a separate 2-L jacketed flask was loaded water (1065 g) and ethylenediamine (390 g). The aqueous solution was heated to 50-55° C. and held. To the 2-cyano-3,5-dimethoxytrifluoroacetanilide/DMF pot residue from the previous step was loaded to the aqueous mixture over at least 15 min. The reaction solution was stirred at 50-55° C. for at least 2 h. A reaction completion check analysis was performed using HPLC. Upon reaction completion the batch was adjusted to 35-37° C. and held for slurry formation. The resulting slurry was cooled slowly to 5-15° C. over at least 2 h. The batch was held at 5-15° C. for 2 h and then the 2-amino-4,6-dimethoxybenzonitrile product was isolated by filtration. The 2-amino-4,6-dimethoxybenzonitrile cake was washed with water to remove the mother liquor. The final wet cake was dried and analyzed by HPLC. The process produced 123 grams of 2-amino-4,6-dimethoxybenzonitrile product [D] in a yield of 88% from the starting 3,5-dimethoxyaniline. $^1$H NMR (acetone-$d_6$) δ 6.03 (d, J=1.9 Hz, 1H), 5.89 (d, J=1.9, 1H), 5.44 (br s, 2H), 3.83 (s, 3H), 3.77 (s, 3H); $^{13}$C NMR (acetone-$d_6$) δ 166.0, 164.1, 154.5, 116.3, 92.3, 88.8, 79.8, 26.2, 55.8. GC-MS: 178.15 (m).

Recrystallization of 2-amino-4,6-dimethoxybenzonitrile [D]

To a 1-L four neck round bottom flask was loaded 2-amino-4,6-dimethoxybenzonitrile (90 g) and isopropyl alcohol (720 mL). The flask was fitted with a condenser and a heating mantle. Carbon (1.8 g) was added to the agitating mixture and the batch was heated to reflux (82-83° C.). The batch was held of 1 h at reflux and then cooled to 75-77° C. and held for at least 6 h. The carbon was then filtered away and the filtrate was collected in a clean 1-L four neck round bottom flask. The filtrate was cooled slowly to 60-62° C. and held until crystallization occurred. The resulting slurry was cooled slowly to 0-5° C. over at least 2 h. The batch was held at 0-5° C. for at least 0.5 h and filtered to harvest the product. The 2-amino-4,6-dimethoxybenzonitrile cake was washed with isopropyl alcohol and dried in a vacuum oven at 50° C. and 22 inches Hg of vacuum. The process produced 83.8 g of purified 2-amino-4,6-dimethoxybenzonitrile (84% yield). [D].

Except as may be expressly otherwise indicated, the article "a" or "an" if and as used herein is not intended to limit, and should not be construed as limiting, the description or a claim to a single element to which the article refers. Rather, the article "a" or "an" if and as used herein is intended to cover one or more such elements, unless the text expressly indicates otherwise.

Each and every patent or other publication or published document referred to in any portion of this specification is incorporated in toto into this disclosure by reference, as if fully set forth herein.

This invention is susceptible to considerable variation within the spirit and scope of the appended claims.

What is claimed is:

1. A compound of Formula I:

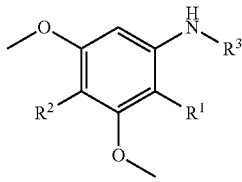

Formula I wherein:
R¹ is selected from Br and CN;
R² is selected from H and Br;
R³ is selected from H and

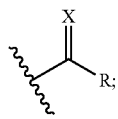

wherein
R is selected from H, CH₃, CF₃, CF₂H, CFH₂, CCl₃, CCl₂H, CClH₂, CBr₃, CBr₂H, and CBrH₂; and
X is selected from O and S;
with the proviso that:
when R¹ is Br and R² is H, then R is not CH₃;
when R¹ is CN then R² is H; and
when R¹ is Br then R³ is

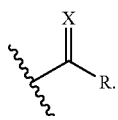

wherein R is not H.

2. A compound according to Formula I-A:

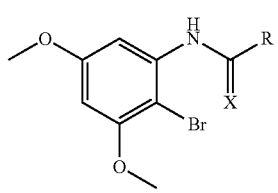

Formula I-A wherein:
R is selected from CF₃, CF₂H, CFH₂, CCl₃, CCl₂H, CClH₂, CBr₃, CBr₂H, and CBrH₂; and
X is selected from O and S.

3. A compound according to Formula I-B:

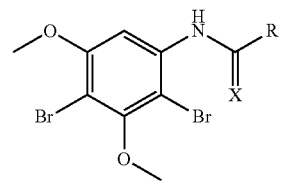

Formula I-B wherein:
R is selected from H, CH₃, CF₃, CF₂H, CFH₂, CCl₃, CCl₂H, CClH₂, CBr₃, CBr₂H, and CBrH₂; and
X is selected from O and S.

4. A compound according to Formula I-C:

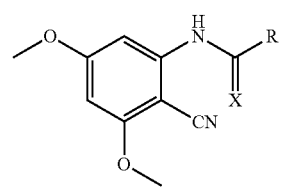

Formula I-C wherein:
R is selected from H, CH₃, CF₃, CF₂H, CFH₂, CCl₃, CCl₂H, CClH₂, CBr₃, CBr₂H, and CBrH₂; and
X is selected from O and S.

5. A compound selected from:
2-bromo-3,5-dimethoxytrifluoroacetanilide,
2,4-dibromo-3,5-dimethoxytrifluoroacetanilide,
2-cyano-3,5-dimethoxytrifuoroacetanilide, and
2-amino-4,6-dimethoxybenzonitrile.

6. A compound according to claim 2, wherein X is oxygen.
7. A compound according to claim 3, wherein X is oxygen.
8. A compound according to claim 4, wherein X is oxygen.
9. A compound according to claim 2, wherein R is selected from CF₃, CF₂H, CFH₂, CCl₃, CCl₂H, and CClH₂.
10. A compound according to claim 3, wherein R is selected from CF₃, CF₂H, CFH₂, CCl₃, CCl₂H, and CClH₂.
11. A compound according to claim 4, wherein R is selected from CF₃, CF₂H, CFH₂, CCl₃, CCl₂H, and CClH₂.
12. The compound according to claim 5, wherein the compound is 2-bromo-3,5-dimethoxytrifluoroacetanilide.
13. The compound according to claim 5, wherein the compound is 2,4-dibromo-3,5-dimethoxytrifluoroacetanilide.
14. The compound according to claim 5, wherein the compound is 2-cyano-3,5-dimethoxytrifuoroacetanilide.
15. The compound according to claim 5, wherein the compound is 2-amino-4,6-dimethoxybenzonitrile.

* * * * *

UNITED STATES PATENT AND TRADEMARK OFFICE
CERTIFICATE OF CORRECTION

PATENT NO. : 8,884,046 B2
APPLICATION NO. : 14/050076
DATED : November 11, 2014
INVENTOR(S) : Mario Emilio Lozanov, Anthony Frank Skufca and Andrew George Zeiler It is certified that error appears in the above-identified patent and that said Letters Patent is hereby corrected as shown below:

In the Claims

Claim 5, Col. 12, Line 40, "2-cyano-3,5-dimethoxytrifuoroacetanilide," should read as --2-cyano-3,5-dimethoxytrifluoroacetanilide,--.

Claim 14, Col. 12, Line 56, "2-cyano-3,5-dimethoxytrifuoroacetanilide." should read as --2-cyano-3,5-dimethoxytrifluoroacetanilide.--.

Signed and Sealed this
Seventeenth Day of March, 2015

Michelle K. Lee
*Director of the United States Patent and Trademark Office*